United States Patent
Cernatescu et al.

(10) Patent No.: US 9,939,393 B2
(45) Date of Patent: Apr. 10, 2018

(54) DETECTION OF CRYSTALLOGRAPHIC PROPERTIES IN AEROSPACE COMPONENTS

(71) Applicant: United Technologies Corporation, Hartford, CT (US)

(72) Inventors: Iuliana Cernatescu, Glastonbury, CT (US); David U. Furrer, Marlborough, CT (US); Venkatarama K. Seetharaman, Rocky Hill, CT (US)

(73) Assignee: United Technologies Corporation, Farmington, CT (US)

( * ) Notice: Subject to any disclaimer, the term of this patent is extended or adjusted under 35 U.S.C. 154(b) by 431 days.

(21) Appl. No.: 14/867,882

(22) Filed: Sep. 28, 2015

(65) Prior Publication Data

US 2017/0089845 A1 Mar. 30, 2017

(51) Int. Cl.
| | |
|---|---|
| *G01N 23/20* | (2006.01) |
| *G01N 23/18* | (2018.01) |
| *G01N 23/087* | (2018.01) |
| *G01N 23/06* | (2018.01) |
| *G01N 23/12* | (2018.01) |
| *G01N 23/08* | (2006.01) |
| *G01N 23/083* | (2018.01) |

(52) U.S. Cl.
CPC ............. *G01N 23/20* (2013.01); *G01N 23/06* (2013.01); *G01N 23/08* (2013.01); *G01N 23/083* (2013.01); *G01N 23/087* (2013.01); *G01N 23/12* (2013.01); *G01N 23/18* (2013.01); *G01N 23/20016* (2013.01); *G01N 23/20025* (2013.01); *G01N 2223/316* (2013.01); *G01N 2223/61* (2013.01); *G01N 2223/6116* (2013.01); *G01N 2223/63* (2013.01); *G01N 2223/6466* (2013.01)

(58) Field of Classification Search
CPC ...... G01N 23/06; G01N 23/08; G01N 23/083; G01N 23/087; G01N 23/12; G01N 23/18; G01N 23/20; G01N 23/20016; G01N 23/20025
USPC .......... 378/57, 58, 70–73, 79, 86–90, 75, 76
See application file for complete search history.

(56) References Cited

U.S. PATENT DOCUMENTS

| | | | |
|---|---|---|---|
| 4,696,024 A | 9/1987 | Pesch | |
| 4,751,722 A * | 6/1988 | Harding | G01N 23/201 378/6 |
| 5,007,072 A * | 4/1991 | Jenkins | G01V 5/0025 378/57 |
| 5,265,144 A * | 11/1993 | Harding | A61B 6/032 378/147 |

(Continued)

OTHER PUBLICATIONS

Wikipedia.org, "Diffraction Topography", downloaded from <https://en.wikipedia.org/wiki/Diffraction_topography> on Aug. 4, 2015.

(Continued)

*Primary Examiner* — Allen C. Ho
(74) *Attorney, Agent, or Firm* — O'Shea Getz P.C.

(57) ABSTRACT

Aspects of the disclosure are directed to an analysis of a material of a component. A radiation source is activated to transmit radiation to the component. A beam pattern is obtained based on the component interfering with the radiation. The beam pattern is compared to a reference beam pattern. An anomaly is detected to exist in the material when the comparison indicates a deviation between the beam pattern and the reference beam pattern.

21 Claims, 5 Drawing Sheets

(56) References Cited

U.S. PATENT DOCUMENTS

| | | | |
|---|---|---|---|
| 5,589,690 A | 12/1996 | Siewert et al. | |
| 5,600,303 A * | 2/1997 | Husseiny | G01V 5/0025 378/57 |
| 5,787,145 A * | 7/1998 | Geus | G01V 5/0025 378/71 |
| 5,908,503 A | 6/1999 | Sumiya | |
| 6,005,913 A | 12/1999 | Zombo | |
| 6,054,712 A * | 4/2000 | Komardin | A61B 6/483 250/363.06 |
| 6,118,850 A * | 9/2000 | Mayo | G01N 23/2076 378/82 |
| 6,122,344 A * | 9/2000 | Beevor | G01N 23/201 378/57 |
| 6,192,104 B1 * | 2/2001 | Adams | G01N 23/203 378/149 |
| 6,442,233 B1 * | 8/2002 | Grodzins | G01N 23/201 378/57 |
| 6,470,067 B1 * | 10/2002 | Harding | A61B 6/032 378/19 |
| 6,621,888 B2 * | 9/2003 | Grodzins | G01N 23/20 378/57 |
| 7,065,175 B2 * | 6/2006 | Green | G01N 23/20 378/57 |
| 7,092,485 B2 * | 8/2006 | Kravis | G01N 23/20 378/57 |
| 7,116,753 B2 * | 10/2006 | Kumakhov | G01N 23/20 378/71 |
| 7,149,279 B2 * | 12/2006 | Kumakhov | G01N 23/20008 378/71 |
| 7,184,517 B2 * | 2/2007 | Kern | G01N 23/2076 378/46 |
| 7,283,613 B2 * | 10/2007 | Harding | G01V 5/0025 378/57 |
| 7,508,500 B2 * | 3/2009 | Rajeswaran | G01N 21/65 250/341.1 |
| 7,558,371 B2 | 7/2009 | Park | |
| 7,564,947 B2 * | 7/2009 | Cernik | G01N 23/046 378/70 |
| 7,590,215 B2 * | 9/2009 | Schlomka | A61B 6/032 378/4 |
| 7,590,220 B1 * | 9/2009 | Lee | G01N 23/2076 378/57 |
| 7,739,075 B2 * | 6/2010 | Sherwood | G01N 23/20 378/70 |
| 7,764,764 B2 * | 7/2010 | Harding | G01N 23/207 378/70 |
| 7,769,134 B1 * | 8/2010 | Adam | G01N 23/20 378/72 |
| 7,796,726 B1 * | 9/2010 | Gendreau | G01N 23/20 378/44 |
| 7,822,177 B2 * | 10/2010 | Bilderback | G01N 23/203 378/76 |
| 7,826,589 B2 * | 11/2010 | Kotowski | G01V 5/0025 378/57 |
| 7,835,495 B2 * | 11/2010 | Harding | G01N 23/20083 378/57 |
| 8,135,205 B2 * | 3/2012 | Jeung | G01N 23/087 382/141 |
| 8,259,901 B1 * | 9/2012 | Kamireddi | B23D 59/001 378/73 |
| 8,300,767 B1 * | 10/2012 | Matsushita | G01N 23/207 378/70 |
| 8,477,905 B2 * | 7/2013 | Belassel | G01N 3/32 378/72 |
| 8,576,985 B2 * | 11/2013 | McClurg | G01N 23/207 378/73 |
| 8,605,858 B2 * | 12/2013 | Singh | G01N 23/207 378/71 |
| 8,625,740 B2 * | 1/2014 | Harding | G01N 23/20 378/207 |
| 8,693,627 B2 * | 4/2014 | Oyaizu | C09K 11/7733 250/483.1 |
| 8,923,480 B2 * | 12/2014 | Wang | G01N 23/20008 378/71 |
| 9,022,651 B2 * | 5/2015 | Kaercher | G01N 23/207 378/207 |
| 9,022,652 B2 * | 5/2015 | Chupas | G01N 23/20025 378/208 |
| 9,063,065 B2 * | 6/2015 | Evans | G01N 23/20083 |
| 9,146,203 B2 * | 9/2015 | Toraya | G01L 1/25 |
| 9,188,551 B2 * | 11/2015 | Harding | G01N 23/201 |
| 9,274,069 B2 * | 3/2016 | Miyao | C01B 33/035 |
| 9,285,329 B2 * | 3/2016 | Ghammraoui | G01N 23/20091 |
| 9,335,281 B2 * | 5/2016 | Marks | G01N 23/20008 |
| 9,513,237 B2 * | 12/2016 | Brescello | G01N 23/20 |
| 9,589,098 B2 * | 3/2017 | Srivastava | G06F 19/00 |
| 9,599,551 B2 * | 3/2017 | Koroteev | G01N 23/083 |
| 9,599,580 B2 * | 3/2017 | Ghammraoui | G01N 23/20091 |
| 9,632,042 B2 * | 4/2017 | Ren | G01N 23/207 |
| 9,726,624 B2 * | 8/2017 | Ryan | G01N 23/2055 |
| 2008/0159479 A1 | 7/2008 | Huang et al. | |
| 2010/0239068 A1 | 9/2010 | Belassel et al. | |
| 2012/0130694 A1 | 5/2012 | Srivastava | |
| 2015/0016594 A1 | 1/2015 | Kaercher | |

OTHER PUBLICATIONS

Wikipedia.org, "Crystallography", downloaded from <https://en.wikipedia.org/wiki/Crystallography> on Aug. 4, 2015.

E.D. Specht, "X-ray microdiffraction analysis of radiation-induced defects in single grains of polycrystalline Fe", Journal of Synchrotron Radiation, doi:10.1107/S0909049509052078, vol. 17, pp. 250-256, Mar. 2010.

Scott A. Speakman, "Introduction to High Resolution X-ray Diffraction of Expitaxial Thin Films", MIT Center for Material Science and Engineering, downloaded from <prism.mit.edu/xray/oldsite/3%20Introduction%20to%20HRXRD.pptx> on Aug. 4, 2015.

Texas A&M University, "Basic X-ray Powder Diffraction (XRPD)", downlaoded from <http://xray.tamu.edu/pdf/notes/intro2xrd.pdf> on Aug. 4, 2015.

J.D. Makinson, "X-Ray Diffraction Signatures of Defects in Nanocrystalline Materials", International Centre for Diffraction Data 2000, Advances in X-ray Analysis, vol. 42, pp. 407-411, 2000.

B. Fultz, "Transmission Electron Microscopy and Diffractometry of Materials, Graduate Texts in Physics", Chapter 1 Diffraction and the X-Ray Powder Diffractometer, DOI10.1007/978-3-642-29761-8_1, Springer-Verlag Berlin Heidelberg, 2013.

Davor Balzar, "X-Ray Diffraction Line Broadening: Modeling and Applications to High-Tc Superconductors", Journal of Research of the National Institute of Standards and Technology, vol. 98, No. 3, May-Jun. 1993, pp. 321-353.

Commission of Powder Diffraction, International Union of Crystallography, Newsletter No. 34, Dec. 2007, ISSN 1591-9552, downloaded from <https://www.fkf.mpg.de/4111943/cpd34.pdf>.

EP search report for EP16190598.9 dated Jan. 24, 2017.

* cited by examiner

DETECTION OF CRYSTALLOGRAPHIC PROPERTIES IN AEROSPACE COMPONENTS

BACKGROUND

In connection with an aircraft, single-crystal (SX) superalloy components provide superior mechanical properties at high temperatures necessary for efficient engine operation. During the manufacture of such components, there are several crystallographic anomalies that may be realized. Such anomalies may include recrystallized grains (RX), secondary grains, freckles, slivers grains, and misaligned primary dendrite.

The anomalies can result in degraded performance or even inoperability of a component. Therefore, detection capabilities of such anomalies are important. In instances where the anomalies mentioned earlier, especially RX, occur in the interior of the component or on a region which is covered by a coating, the detection of the anomalies by non-destructive techniques (with respect to the component) is not possible with conventional technology.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of the disclosure are directed to a method for analyzing a material of a component, comprising: activating a radiation source to transmit radiation to the component, obtaining a beam pattern based on the component interfering with the radiation, comparing the beam pattern to a reference beam pattern, and detecting that an anomaly exists in the material when the comparison indicates a deviation between the beam pattern and the reference beam pattern. In some embodiments, the component is associated with an engine of an aircraft. In some embodiments, the component includes a turbine blade. In some embodiments, the reference beam pattern is expected to be emanated by the component when the component is subject to the radiation. In some embodiments, the component is associated with a semiconductor. In some embodiments, the component has a coating. In some embodiments, the radiation comprises x-ray radiation. In some embodiments, the method further comprises specifying the anomaly in terms of at least one of: a crystalline orientation of the material, a location of the anomaly, or a size of the anomaly. In some embodiments, the method further comprises rejecting the component when the deviation is greater than a threshold. In some embodiments, the method further comprises repairing the component when the deviation is greater than a threshold.

Aspects of the disclosure are directed to a system for analyzing a material of a component, comprising: a control computer configured to store a reference model of a first beam pattern that is expected to be emanated by the component when the component is subject to input radiation, a source configured to transmit the input radiation to the component, and a detector configured to obtain a second beam pattern based on the exposure of the component to the input radiation, where at least one of the control computer or the detector is configured to: compare the second beam pattern to the first beam pattern, and detect that an anomaly exists in the material when the comparison indicates a deviation between the second beam pattern and the first beam pattern. In some embodiments, the input radiation comprises x-ray radiation. In some embodiments, the x-ray radiation has an energy within a range of 40 KeV-600 KeV. In some embodiments, the system comprises a collimation system configured to control a size of the input radiation to within a range of 0.05 mm-10 mm. In some embodiments, the system further comprises a sample stage configured to load a plurality of components, the plurality of components including the component. In some embodiments, the control computer is configured to issue a command to the sample stage to orient the component with respect to at least one of the source or the detector. In some embodiments, the command directs the sample stage to orient the component in terms of at least one of a distance or an angle with respect to the at least one of the source or the detector. In some embodiments, the sample stage has between one and six axes of mobility. In some embodiments, the at least one of the control computer or the detector is configured to specify the anomaly in terms of at least one of: a crystalline orientation of the material, a location of the anomaly, or a size of the anomaly.

Aspects of the disclosure are directed to an apparatus for analyzing a material of a blade of an aircraft engine, comprising: at least one processor, and memory having instructions stored thereon that, when executed by the at least one processor, cause the apparatus to: store a reference model of a first beam pattern that is expected to be emanated by the blade when the blade is subject to input radiation, activate a source to cause the source to transmit the input radiation, obtain a second beam pattern based on the blade interfering with the input radiation, compare the second beam pattern to the first beam pattern, and detect that an anomaly exists in the material when the comparison indicates a deviation between the second beam pattern and the first beam pattern. In some embodiments, the reference model of the first beam pattern accounts for a coating that is applied to the blade, and the instructions, when executed by the at least one processor, further cause the apparatus to: specify the anomaly in terms of at least one of a crystalline orientation of the material, a location of the anomaly, or a size of the anomaly, and indicate that the blade is rejected when the deviation is greater than a threshold.

BRIEF DESCRIPTION OF THE DRAWINGS

The present disclosure is illustrated by way of example and not limited in the accompanying figures in which like reference numerals indicate similar elements.

DETAILED DESCRIPTION

It is noted that various connections are set forth between elements in the following description and in the drawings (the contents of which are included in this disclosure by way of reference). It is noted that these connections are general and, unless specified otherwise, may be direct or indirect and that this specification is not intended to be limiting in this respect. A coupling between two or more entities may refer to a direct connection or an indirect connection. An indirect connection may incorporate one or more intervening entities.

In accordance with various aspects of the disclosure, apparatuses, systems, and methods are described for non-destructively detecting crystalline domains having an orientation that differs from a matrix in a nominally single-crystal (SX) component/structure by use of high energy X-rays. An RX defect can be detected based on measured orientation difference between the area with defect and adjacent defect free area using one or more thresholds. For example, in some embodiments the techniques that are described herein may be applied to volumes that are based on or defined by computational modeling, where the computational modeling may serve as a basis for the thresholds. Still further, in some embodiments a "coupon" or other portion or segment that is characteristic of the volume may be evaluated or serve as a baseline for establishing a reference specification or model.

Aspects of the disclosure may be used to ensure that grains of material stay on-axis, which may assist in promoting strength/toughness and creep resistance. Additionally, aspects of the disclosure may provide for a determination of mal-oriented grains (MOG), in a nondestructive manner. In some embodiments, a determination may be made whether MOG due to recrystallization has occurred during production or when a component has been placed into service.

In some embodiments, a controlled size X-ray beam may be transmitted and directed toward and through a component and diffraction data may be obtained based on the transmitted X-ray. A mapping of the diffraction data, potentially based on one or more reference specification or models, may be obtained to determine if a crystalline orientation associated with the component differs from a specification in an amount that exceeds one or more thresholds.

In some embodiments, diffraction data may be analyzed to determine if a single of multiple grains exist in interrogated volumes.

In some embodiments, a scanning or mapping of an x-ray beam may be provided throughout the entirety or a portion of a component to assess each incremental volume for single or multiple grain appearance.

In some embodiments, computational models of solidification processes and/or heat treatments may be used to determine volumes exposed to a risk of recrystallization, where the risk may be based on the use of one or more thresholds.

In some embodiments, computational models and X-ray characterizations of nominally SX materials or components may be determined/obtained. Such features may be used to enhance the rate or probability of detecting secondary grains.

Figure 1:
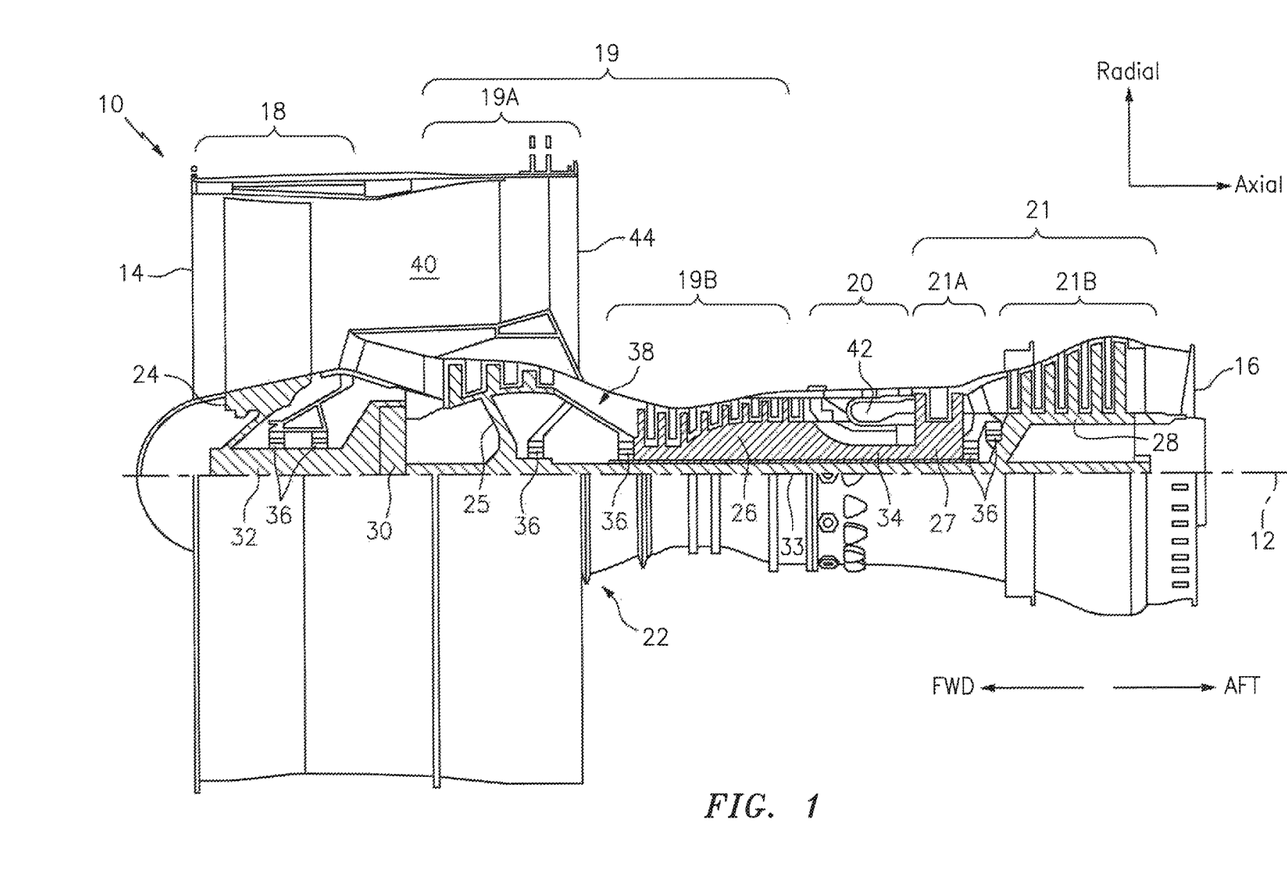
FIG. 1 is a side cutaway illustration of a geared turbine engine.

Aspects of the disclosure may be applied in connection with one or more components of a gas turbine engine. FIG. 1 is a side cutaway illustration of a geared turbine engine 10. The geared turbine engine 10 extends along an axial centerline 12 between an upstream airflow inlet 14 and a downstream airflow exhaust 16. The geared turbine engine 10 includes a fan section 18, a compressor section 19, a combustor section 20 and a turbine section 21. The compressor section 19 includes a low pressure compressor (LPC) section 19A and a high pressure compressor (HPC) section 19B. The turbine section 21 includes a high pressure turbine (HPT) section 21A and a low pressure turbine (LPT) section 21B.

The engine sections 18-21 are arranged sequentially along the centerline 12 within an engine housing 22. Each of the engine sections 18-19B, 21A and 21B includes a respective rotor 24-28. Each of these rotors 24-28 includes a plurality of rotor blades arranged circumferentially around and connected to one or more respective rotor disks. The rotor blades, for example, may be formed integral with or mechanically fastened, welded, brazed, adhered and/or otherwise attached to the respective rotor disk(s).

The fan rotor 24 is connected to a gear train 30, for example, through a fan shaft 32. The gear train 30 and the LPC rotor 25 are connected to and driven by the LPT rotor 28 through a low speed shaft 33. The HPC rotor 26 is connected to and driven by the HPT rotor 27 through a high speed shaft 34. The shafts 32-34 are rotatably supported by a plurality of bearings 36; e.g., rolling element and/or thrust bearings. Each of these bearings 36 is connected to the engine housing 22 by at least one stationary structure such as, for example, an annular support strut.

During operation, air enters the turbine engine 10 through the airflow inlet 14, and is directed through the fan section 18 and into a core gas path 38 and a bypass gas path 40. The air within the core gas path 38 may be referred to as "core air". The air within the bypass gas path 40 may be referred to as "bypass air". The core air is directed through the engine sections 19-21, and exits the turbine engine 10 through the airflow exhaust 16 to provide forward engine thrust. Within the combustor section 20, fuel is injected into a combustion chamber 42 and mixed with compressed core air. This fuel-core air mixture is ignited to power the turbine engine 10. The bypass air is directed through the bypass gas path 40 and out of the turbine engine 10 through a bypass nozzle 44 to provide additional forward engine thrust. This additional forward engine thrust may account for a majority (e.g., more than 70 percent) of total engine thrust. Alternatively, at least some of the bypass air may be directed out of the turbine engine 10 through a thrust reverser to provide reverse engine thrust.

FIG. 1 represents one possible configuration for an engine 10. Aspects of the disclosure may be applied in connection with other environments, including additional configurations for an engine of an aircraft.

Aspects of the disclosure may be used to detect crystallographic anomalies in one or more components, such as for example a component of an engine. For example, aspects of the disclosure may be used to detect anomalies in SX blades of the engine 10. The detection may be based on a use of one or more of: (1) process modeling tools, (2) a system for diffraction data collection, (3) logic configured to align components in the diffraction system, (4) logic configured to obtain and analyze data, and (5) logic configured to determine whether an anomaly exists in an amount greater than a threshold.

Figure 2:
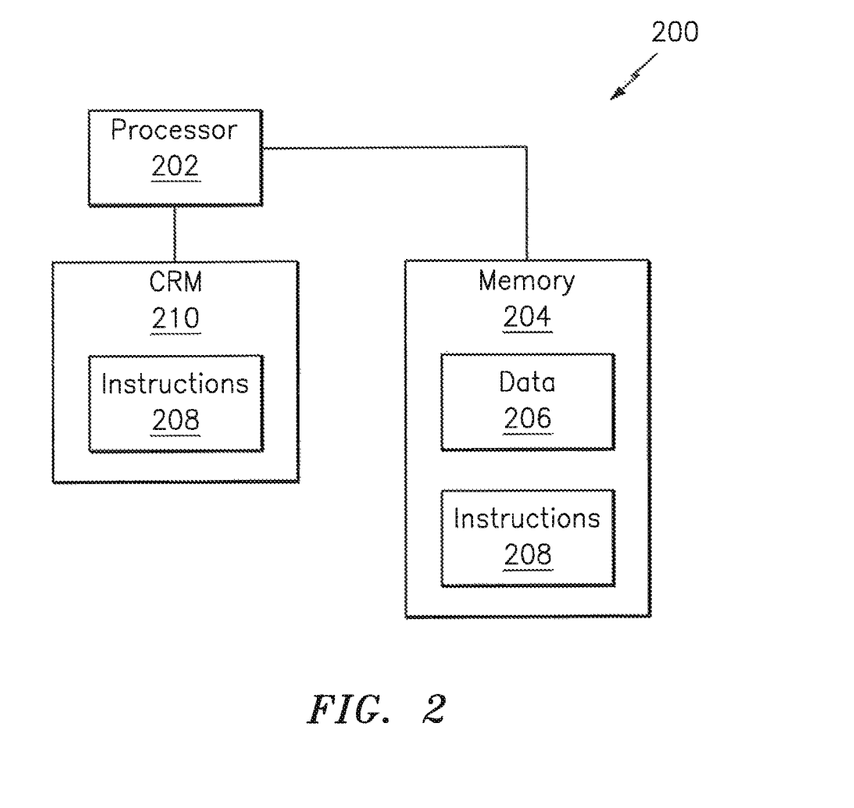
FIG. 2 illustrates a computing system.

Referring to FIG. 2, an illustrative computing environment is shown. A system 200 may include one or more processors (generally shown by a processor 202) and a memory 204. The memory 204 may store data 206 and/or instructions 208. The system 200 may include a computer-readable medium (CRM) 210 that may store some or all of the instructions 208. The CRM 210 may include a transitory and/or non-transitory computer-readable medium.

The data 206 may include one or more parameters that may be associated with a component (e.g., a blade). For example, the parameters may be based on an actual component that is undergoing analysis or a reference component/specification as is described further below. The parameters may be used to determine/detect a crystalline orientation associated with the component and/or determine/detect whether that orientation differs from the reference specification in an amount greater than a threshold.

The instructions 208, when executed by the processor 202, may cause the system 200 to perform one or more methodological acts or processes, such as those described herein. As an example, execution of the instructions 208 may cause the system 200 to determine/detect a crystalline orientation associated with a component and/or determine/detect whether that orientation differs from a specification in an amount greater than a threshold.

Figure 3A:
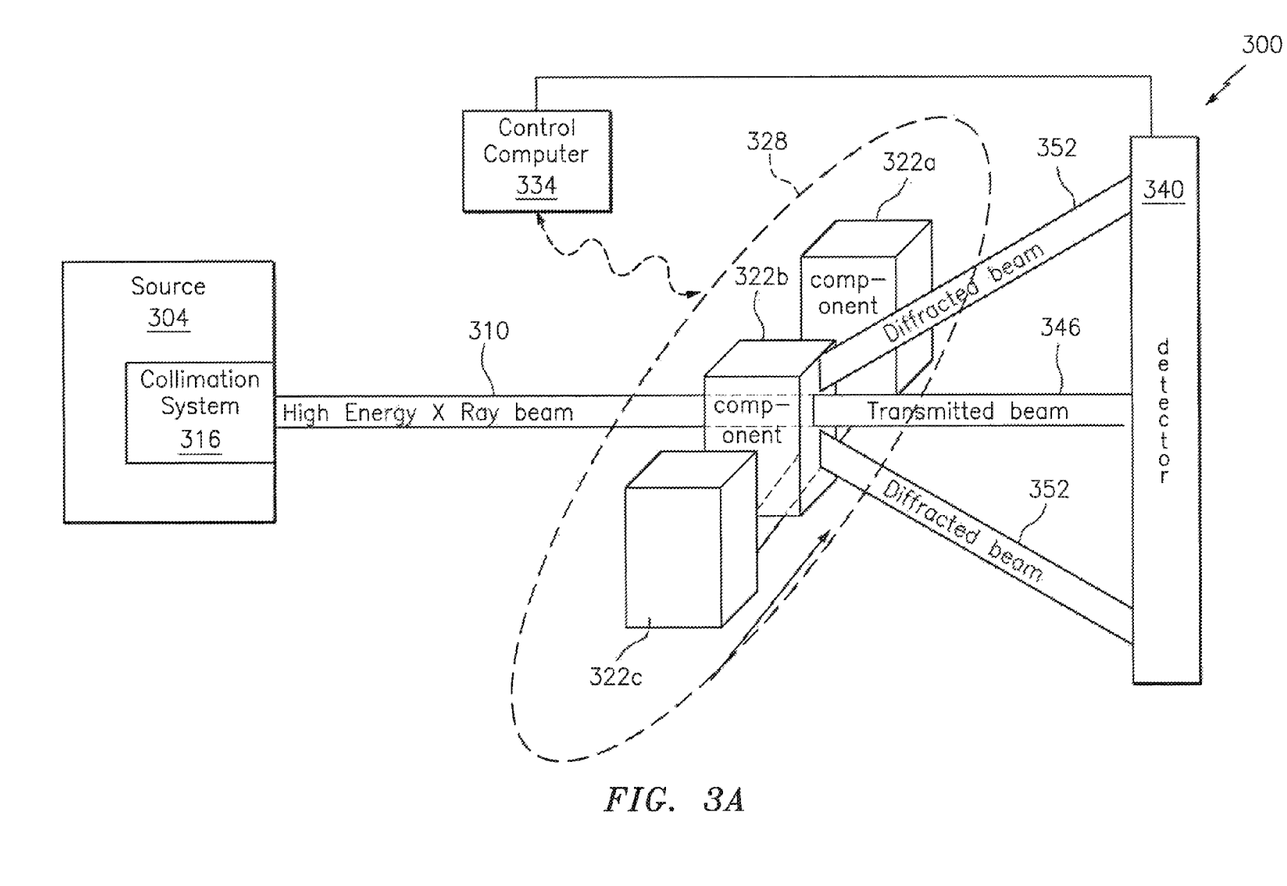
FIG. 3A illustrates a system configured to detect an anomaly associated with one or more components.

Referring now to FIG. 3A, a system 300 in accordance with aspects of the disclosure is shown. The system 300 may be used to detect a crystalline orientation associated with a component and/or detect whether that orientation differs from a specification in an amount greater than a threshold.

The system 300 may include a source 304. The source 304 may generate and transmit one or more forms of radiation, such as for example neutron, gamma rays, or x-ray, hereinafter input radiation 310. In some non-limiting embodiments, the input radiation 310 may have an associated energy in the range of 40-600 KeV. The energy of the source 304 may be selected to ensure that signals/beams of sufficiently high quality (e.g., sufficiently high signal-to-noise ratio) are obtained by a detector e.g., the detector 340 as shown). In some embodiments, the detector 340 may be configured as one or more area detector arrays.

The source 304 may include, or be associated with, a collimation system 316. The collimation system 316 may be configured to control the size of the input radiation 310. In some embodiments, the input radiation 310 may range in size (e.g., diameter as projected from the source 304) from 0.05 mm to 10 mm, +/−0.02 mm. The particular size, or even wavelength, that is used for the input radiation 310 may be a function of the resolution that is needed in a particular application context. For example, aspects of the disclosure may be used to detect anomalies on the order of 25 micrometers, and thus the characteristics of the input radiation 310 (e.g., power, size, wavelength, frequency, etc.) may be selected to optimize detections of this order.

While the collimation system 316 is shown in FIG. 3A as being included in the source 304, in some embodiments the collimation system 316 may be a separate device relative to the source 304.

The input radiation 310 may impinge on/interface to one or more components, such as for example components 322a, 322b, and 322c. In some embodiments, one or more of the components 322a-322c may include a blade. The components 322a-322c may be associated with a sample stage (denoted as reference character 328 in FIG. 3A). The sample stage 328 may include one or more axes of mobility, such as for example one to six axes of mobility. The selection, configuration, or orientation of the axes may be used for providing a particular alignment of the components 322a, 322b, or 322c, may be used to enable a three-dimensional analysis of the components 322a-322c, may be used to examine a particular surface/face of one or more of the components 322a-322c, etc. The sample stage 328 may include slots for the components 322a-322c to be loaded into. As part of the loading, the components 322a-322c may be aligned, e.g., on a collective or individual basis.

In some embodiments, the operations (e.g., a loading or movement) associated with the sample stage 328 may be controlled by a computing platform/control computer 334. The sample stage 328 and/or the control computer 334 may include one or more of the devices shown and described above in connection with FIG. 2.

In some embodiments, the control computer 334 may issue commands to the sample stage 328 to control the sample stage 328. In some embodiments, the control computer 334 and the sample stage 328 may be communicatively coupled to one another to facilitate the transmission of the commands. The communication may adhere to one or more techniques, protocols, standards, etc. The communication may be wired and/or wireless. In some embodiments, feedback regarding the operations performed by the sample stage 328 may be transmitted from the sample stage 328 to the control computer 334, which may be used to facilitate closed-loop communication between the sample stage 328 and the control computer 334.

Figure 3B:
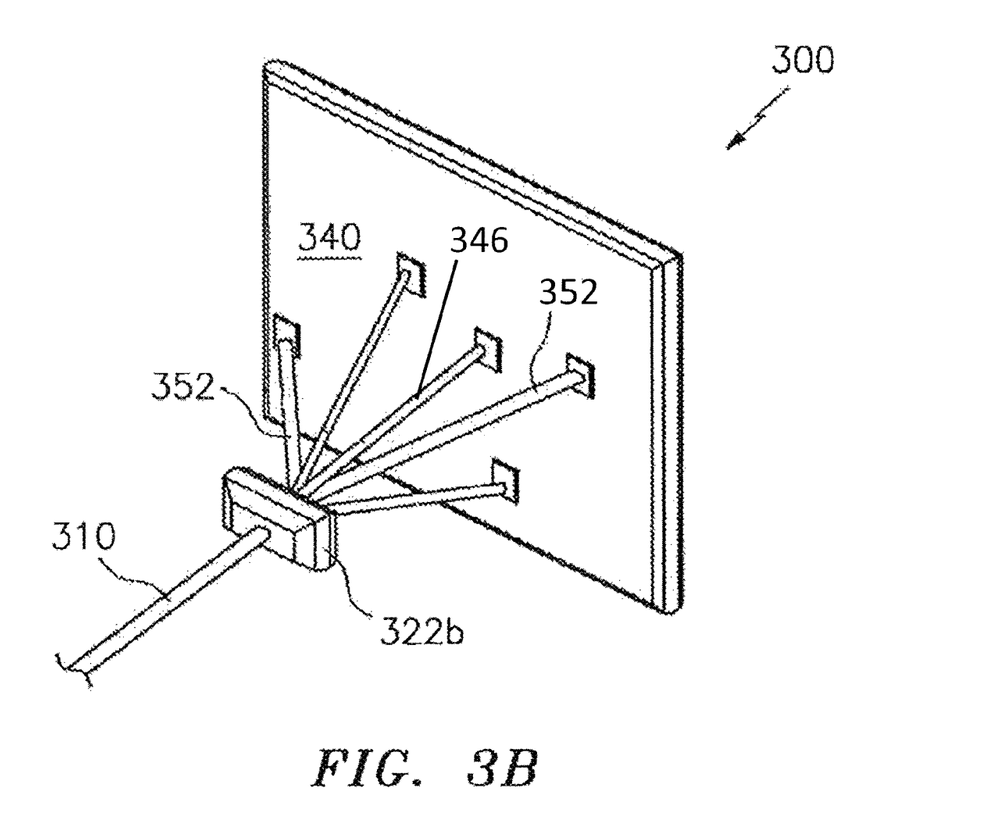
FIG. 3B illustrates a perspective view of a portion of the system of FIG. 3A.

In FIG. 3A, the component 322b is shown as being aligned with the input radiation 310, such that data associated with the component 322b may be obtained. The data may be obtained by a detector 340. The data may be based on one or more beams emanating from the component 322b. For example, the data may be based on a transmitted beam 346 and one or more diffracted beams 352. The detector 340 may be mounted on a device that enables a change in distance between the detector 340 and the components 322a-322c and a change in angle between the transmitted beam 346 and the normal to the detector 340. In some embodiments, the detector 340 may be configured to move and/or the sample stage 328 may be configured to move to alter the distance and/or angle as described above. Referring to FIG. 3B, in one non-limiting example when the input radiation 310 is projected incident to the component 322b, a resulting pattern of the transmitted beam 346 and/or the diffracted beams 352 may result, with the pattern being detected by the detector 340 and being the basis for the collected data. The pattern may pertain to a surface and/or volume of the component that is being analyzed (illustratively, the component 322b in FIG. 3B).

The data obtained via the transmitted beam 346 and/or the diffracted beam(s) 352 may be compared by the detector 340 and/or the control computer 334 with a reference specification or model beam pattern to determine/detect a crystalline orientation associated with the component 322b and/or determine/detect whether that orientation differs from the reference specification/model beam pattern in an amount greater than a threshold. For example, if the component 322b was nominally manufactured/fabricated of a SX material (e.g., a nickel-based material), the potential presence of at least one other crystal/grain in the component 322b as the component 322b was actually manufactured may result in a deviation in the transmitted beam 346 and/or the diffracted beam(s) 352 emanating from the component 322b. Thus, the pattern detected by the detector 340 may vary from the reference specification or model beam pattern.

In some embodiments, a deviation in the actual pattern from the reference pattern in an amount less than a first threshold (e.g., a low angle deviation) may be indicative of low stress, such that the component may be acceptable for use. A deviation in the actual pattern from the reference pattern in an amount greater than a second threshold (e.g., a high angle deviation) may be indicative of a component that is unacceptable for use. The first and second thresholds in this example may be the same.

This deviation in the transmitted beam 346 and/or the diffracted beam(s) 352 may be used to determine/detect that an anomaly exists in the crystalline orientation of the component 322b. Still further, the deviation may be quantified in terms of, e.g., size and location of the anomaly to determine exactly what the crystalline structure and orientation of the component 322b is. Such information may be used to determine how much stress may exist at the crystal/grain-boundaries. As described above, if the stress is less than a threshold, the component 322b may be accepted for use. On the other hand, if the stress exceeds a threshold, the component 322b may be discarded, repaired, or subject to some other action.

While the examples described above related to an assessment of the component 322b in terms of how it was manufactured/fabricated, aspects of the disclosure may be applied to components that are already in-service or in-the-field.

Such in-service components may have materials added to them beyond the SX material that the component is constructed of. For example, aircraft engine components may be subjected to one or more coatings (e.g., a ceramic coating), potentially as part of a thermal barrier coating (TBC) procedure, before they are deployed on the engine. The system 300 may be used in conjunction with such components as well; any modifications that are needed might only need to be made with respect to the reference specifications/models that are used for the component to account for the presence of the additional materials/coatings that are included.

Still further, the SX-material of an in-service component may undergo a material change/transformation over time. Such a transformation may be at least partially based on exposure of the component to environmental conditions (e.g., temperature, vibration, etc.). Accordingly, the system 300 may be used to determine/detect a modification to the component crystalline orientation or material. If the component is subject to analysis by the system 300 over time, changes may be recorded over that same time period. Such information may be analyzed to determine the useful/operative lifetime of the component.

Figure 4:
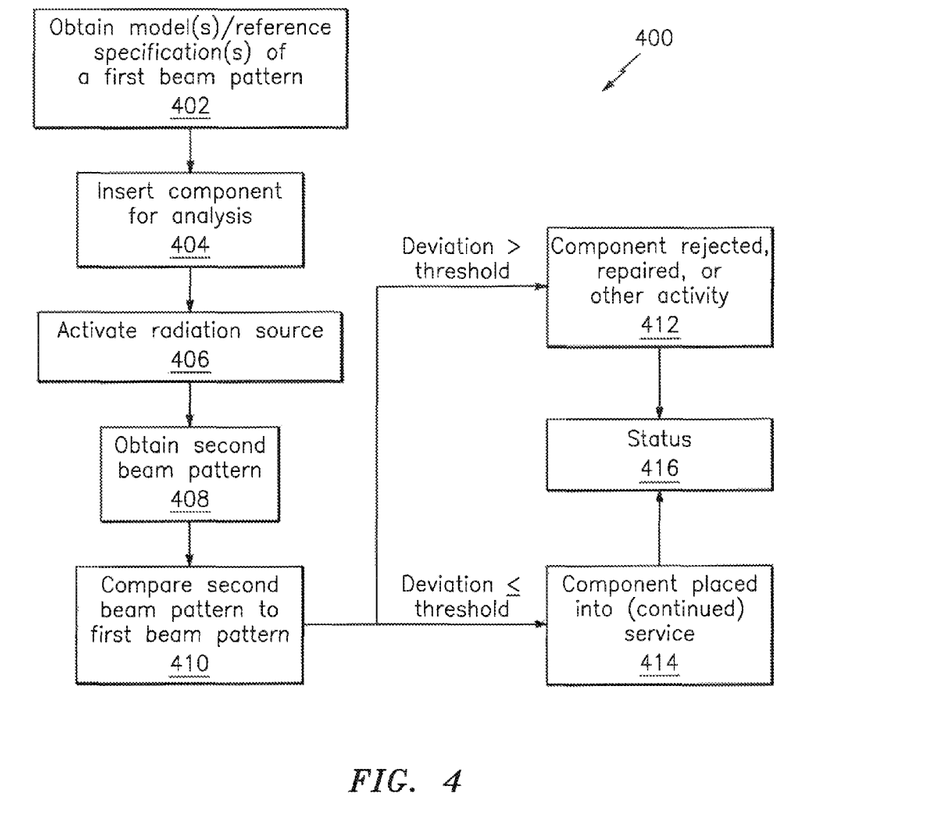
FIG. 4 illustrates a flowchart of a method to detect an anomaly associated with a component.

Referring now to FIG. 4, a flowchart of an exemplary method 400 is shown. The method 400 may be executed by one or more devices or systems, such as those that are described herein. For example, the method 400 may be executed by the sample stage 328 and/or the control computer 334 of the system 300 to analyze one or more components (e.g., components 322a-322c).

In block 402, one or more models of a component may be obtained. A model may include, or be associated with, a reference specification of a beam pattern (e.g., a first beam pattern) that is expected to emanate from the component when the component is subjected to a stimulus or input radiation 310 (e.g., x-rays). The reference specification/model may be based on a profile/dimension of the component, an indication of one or more materials that were used in fabricating/manufacturing the component (inclusive of any coatings that may be applied to the component), a profile of a radiation source that is used, or other factors.

In block 404, a component may be inserted into the system 300 for analysis. For example, a component may be seated/aligned in the sample stage 328.

In block 406, a source 304 may be activated to transmit input radiation 310 (e.g., x-rays) towards the component.

In block 408, a beam pattern (e.g., a second beam pattern) that includes one or more beams emanating from the component (based on the radiation transmitted in block 406) may be obtained by a detector 340.

In block 410, the second beam pattern obtained as part of block 408 may be compared with the first beam pattern of the reference specification/model to determine if the second beam pattern deviates from the first beam pattern in an amount greater than a threshold.

If the deviation in block 410 is greater than the threshold, an anomaly may exist and the component may be subjected to rejection, repair, or some other activity in block 412, potentially based on the extent or degree of the deviation.

On the other hand, if the deviation in block 410 is less than or equal to the threshold the component may be placed into service, or continue to be used in-service, in block 414.

In block 416, a status (e.g., a report) of the analysis performed in connection with blocks 410-414 may be provided. For example, a pass (e.g., block 414) or fail (e.g., block 412) status may be generated as part of block 416 for the component. Other types of status may be generated and/or recorded as part of block 416.

The method 400 is illustrative. In some embodiments, the blocks may execute in an order or sequence that is different from what is shown in FIG. 4. In some embodiments, additional blocks or operations that are not shown may be included. In some embodiments, one or more of the blocks may be optional. In some embodiments, at least a portion of the method 400 may be automated. Such features may be used to process a large number of components, potentially as part of an assembly line. In this respect, the method 400 may be executed repeatedly or as part of a larger loop or algorithm for each component that is to be analyzed.

Aspects of the disclosure may be used to detect anomalies in a component. Such anomalies might otherwise go unnoticed without the teachings of this disclosure. For example, aspects of the disclosure may be used to detect anomalies that may exist within the interior of a component without having to decompose/destruct the component and without having to remove any additional materials (e.g., coatings) that may have been intentionally applied to the component. Still further, when an anomaly is detected the degree/extent of the deviation may be quantified to determine any activities/actions that may need to be taken based on the anomaly.

While some of the examples described herein related to components used in connection with an aircraft engine, aspects of the disclosure may be used in other application environments/contexts. For example, aspects of the disclosure may be used to characterize one or more portions of a semiconductor. If the semiconductor is made of a first/primary material (e.g., silicon), aspects of the disclosure may be used to assess the crystalline properties of the first material even in the presence of one or more additional materials (e.g., gallium arsenide).

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one of ordinary skill in the art will appreciate that the steps described in conjunction with the illustrative figures may be performed in other than the recited order, and that one or more steps illustrated may be optional in accordance with aspects of the disclosure.

What is claimed is:

1. A method for analyzing a material of a component, comprising:
   activating a radiation source to transmit radiation to the component;
   obtaining a beam pattern based on the component interfering with the radiation;
   comparing the beam pattern to a reference beam pattern; and
   detecting that an anomaly exists in the material when the comparing of the beam pattern to the reference beam pattern indicates a deviation between the beam pattern and the reference beam pattern.

2. The method of claim 1, wherein the component is associated with an engine of an aircraft.

3. The method of claim 2, wherein the component includes a turbine blade.

4. The method of claim 1, wherein the reference beam pattern is expected to be emanated by the component when the component is subject to the radiation.

5. The method of claim 1, wherein the component is associated with a semiconductor.

6. The method of claim 1, wherein the component comprises a coating.

7. The method of claim 1, wherein the radiation comprises x-ray radiation.

8. The method of claim 1, further comprising:
specifying the anomaly in terms of at least one of: a crystalline orientation of the material, a location of the anomaly, or a size of the anomaly.

9. The method of claim 1, further comprising:
rejecting the component when the deviation is greater than a threshold.

10. The method of claim 1, further comprising:
repairing the component when the deviation is greater than a threshold.

11. A system for analyzing a material of a component, comprising:
a control computer configured to store a reference model of a first beam pattern that is expected to be emanated by the component when the component is subject to input radiation;
a source configured to transmit input radiation to the component; and
a detector configured to obtain a second beam pattern based on an exposure of the component to the input radiation;
wherein at least one of the control computer or the detector is configured to:
detect that an anomaly exists in the material when a comparison of the second beam pattern to the first beam pattern indicates a deviation between the second beam pattern and the first beam pattern.

12. The system of claim 11, wherein the input radiation comprises x-ray radiation.

13. The system of claim 12, wherein the x-ray radiation has an energy within a range of 40 keV-600 keV.

14. The system of claim 12, further comprising:
a collimation system configured to control a size of the input radiation to within a range of 0.05 mm-10 mm.

15. The system of claim 11, further comprising:
a sample stage configured to load a plurality of components, the plurality of components including the component.

16. The system of claim 15, wherein the control computer is configured to issue a command to the sample stage to orient the component with respect to at least one of the source or the detector.

17. The system of claim 16, wherein the command directs the sample stage to orient the component in teinis of at least one of a distance or an angle with respect to the at least one of the source or the detector.

18. The system of claim 15, wherein the sample stage has between one and six axes of mobility.

19. The system of claim 11, wherein the at least one of the control computer or the detector is configured to specify the anomaly in terms of at least one of: a crystalline orientation of the material, a location of the anomaly, or a size of the anomaly.

20. An apparatus for analyzing a material of a blade of an aircraft engine, comprising:
at least one processor; and
memory having instructions stored thereon that, when executed by the at least one processor, cause the at least one processor to:
store a reference model of a first beam pattern that is expected to be emanated by the blade when the blade is subject to input radiation;
activate a source to cause the source to transmit input radiation;
obtain a second beam pattern based on the blade interfering with the input radiation; and
detect that an anomaly exists in the material when a comparison of the second beam pattern to the first beam pattern indicates a deviation between the second beam pattern and the first beam pattern.

21. The apparatus of claim 20, wherein the reference model of the first beam pattern accounts for a coating that is applied to the blade, and wherein the instructions, when executed by the at least one processor, further cause the at least one processor to:
specify the anomaly in terms of at least one of: a crystalline orientation of the material, a location of the anomaly, or a size of the anomaly; and
indicate that the blade is rejected when the deviation is greater than a threshold.

* * * * *

UNITED STATES PATENT AND TRADEMARK OFFICE
CERTIFICATE OF CORRECTION

PATENT NO. : 9,939,393 B2
APPLICATION NO. : 14/867882
DATED : April 10, 2018
INVENTOR(S) : Cernatescu et al.

Page 1 of 1

It is certified that error appears in the above-identified patent and that said Letters Patent is hereby corrected as shown below:

In the Claims

Column 10, Line 10, please delete "teinis" and insert --terms--.

Signed and Sealed this
Fifteenth Day of May, 2018

Andrei Iancu
*Director of the United States Patent and Trademark Office*